US009949902B2

(12) United States Patent
Mundschau et al.

(10) Patent No.: US 9,949,902 B2
(45) Date of Patent: Apr. 24, 2018

(54) STABLE EMULSION FOR PREVENTION OF SKIN IRRITATION AND ITEMS USING SAME

(71) Applicant: Kimberly-Clark Worldwide, Inc., Neenah, WI (US)

(72) Inventors: Stacy Averic Mundschau, Weyauwega, WI (US); Philip Eugene Kieffer, Winneconne, WI (US); Corey Thomas Cunningham, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 585 days.

(21) Appl. No.: 13/925,316

(22) Filed: Jun. 24, 2013

(65) Prior Publication Data

US 2014/0004164 A1 Jan. 2, 2014

Related U.S. Application Data

(60) Provisional application No. 61/666,382, filed on Jun. 29, 2012.

(51) Int. Cl.

| | |
|---|---|
| ***A61K 8/92*** | (2006.01) |
| ***A61Q 19/00*** | (2006.01) |
| ***A61K 8/06*** | (2006.01) |
| ***A61K 8/27*** | (2006.01) |
| ***A61K 8/34*** | (2006.01) |
| ***A61K 8/37*** | (2006.01) |
| ***A61K 8/41*** | (2006.01) |
| ***A61K 8/49*** | (2006.01) |
| ***A61K 8/55*** | (2006.01) |
| ***A61K 8/60*** | (2006.01) |
| ***A61K 8/73*** | (2006.01) |
| ***A61K 8/891*** | (2006.01) |
| ***A61K 8/02*** | (2006.01) |

(52) U.S. Cl.

CPC .............. *A61K 8/06* (2013.01); *A61K 8/0208* (2013.01); *A61K 8/062* (2013.01); *A61K 8/27* (2013.01); *A61K 8/342* (2013.01); *A61K 8/37* (2013.01); *A61K 8/416* (2013.01); *A61K 8/4973* (2013.01); *A61K 8/55* (2013.01); *A61K 8/602* (2013.01); *A61K 8/73* (2013.01); *A61K 8/733* (2013.01); *A61K 8/737* (2013.01); *A61K 8/891* (2013.01); *A61K 8/92* (2013.01); *A61Q 19/00* (2013.01); *A61K 2800/594* (2013.01); *A61K 2800/75* (2013.01)

(58) Field of Classification Search

CPC ........ A61K 8/0208; A61K 8/062; A61K 8/06; A61K 8/25; A61K 8/27; A61K 8/92; A61K 8/342; A61K 8/416; A61K 8/4973; A61K 8/55; A61K 8/602; A61K 8/73; A61K 8/733; A61K 8/737; A61K 8/891; A61K 2800/594; A61K 2800/75; A61Q 19/00

See application file for complete search history.

(56) References Cited

U.S. PATENT DOCUMENTS

| | | | | |
|---|---|---|---|---|
| 3,896,807 | A | 7/1975 | Buchalter | |
| 4,382,919 | A | 5/1983 | Alonso et al. | |
| 4,690,821 | A | 9/1987 | Smith et al. | |
| 4,772,501 | A * | 9/1988 | Johnson et al. | 428/74 |
| 4,806,572 | A | 2/1989 | Kellett | |
| 4,904,524 | A | 2/1990 | Yoh | |
| 5,110,593 | A | 5/1992 | Benford | |
| 5,362,488 | A | 11/1994 | Sibley et al. | |
| 5,385,748 | A * | 1/1995 | Bunger et al. | 426/590 |
| 5,436,007 | A | 7/1995 | Hartung et al. | |
| 5,525,346 | A | 6/1996 | Hartung et al. | |
| 5,585,104 | A | 12/1996 | Ha et al. | |
| 5,643,588 | A | 7/1997 | Roe et al. | |
| 5,648,083 | A | 7/1997 | Blieszner et al. | |
| 5,858,335 | A | 1/1999 | Lucas et al. | |
| 5,861,145 | A | 1/1999 | Lucas et al. | |
| 5,861,147 | A | 1/1999 | Dodd et al. | |
| 5,863,663 | A | 1/1999 | Mackey et al. | |
| 5,874,067 | A | 2/1999 | Lucas et al. | |
| 5,968,025 | A | 10/1999 | Roe et al. | |
| 5,985,177 | A | 11/1999 | Yoshida et al. | |
| 6,083,854 | A | 7/2000 | Bogdanski et al. | |
| 6,103,245 | A | 8/2000 | Clark et al. | |
| 6,153,208 | A | 11/2000 | McAtee et al. | |

(Continued)

FOREIGN PATENT DOCUMENTS

| | | | |
|---|---|---|---|
| EP | 0 117 613 | B1 | 6/1990 |
| EP | 0 564 307 | A1 | 10/1993 |

(Continued)

OTHER PUBLICATIONS

Kamath et al. "Spunlace (hydroentanglement)" (Apr. 2004), [online], retrieved on [Sep. 2, 2014] from URL <http://www.engr.utk.edu/mse/Textiles/Spunlace.htm>.*
Runhe Sea Melody Wet Wipes, sold on Mintel web page "http://www.gnpd.com", Jun. 2010, 2 pages.

*Primary Examiner* — John Pak
*Assistant Examiner* — Daniel Branson
(74) *Attorney, Agent, or Firm* — Kimberly-Clark Worldwide, Inc.

(57) ABSTRACT

An emulsion suitable for incorporation into wet wipes used to clean urine and fecal matter from the skin. The emulsion includes silicone oil and water-soluble zinc salt such as zinc chloride and zinc sulfate. Phase separation is prevented with an emulsification system that includes a gum blend and salt-tolerant emulsifier. The gum blend includes at least one gum and propylene glycol alginate.

15 Claims, No Drawings

(56) References Cited

U.S. PATENT DOCUMENTS

| | | | | |
|---|---|---|---|---|
| 6,280,757 | B1 | 8/2001 | McAtee et al. | |
| 6,284,257 | B1 | 9/2001 | Khayat et al. | |
| 6,287,581 | B1 | 9/2001 | Krzysik et al. | |
| 6,303,119 | B1 | 10/2001 | Weisgerber et al. | |
| 6,352,700 | B1 | 3/2002 | Luu et al. | |
| 6,410,039 | B1 | 6/2002 | Walker | |
| 6,416,788 | B1 | 7/2002 | Barr | |
| 6,419,963 | B1 | 7/2002 | Niazi | |
| 6,436,418 | B1 | 8/2002 | Sheldon et al. | |
| 6,440,437 | B1 | 8/2002 | Krzysik et al. | |
| 6,461,601 | B1 | 10/2002 | Stoddart et al. | |
| 6,488,943 | B1 | 12/2002 | Beerse et al. | |
| 6,500,443 | B1 | 12/2002 | Otts et al. | |
| 6,503,524 | B1 | 1/2003 | Tyrrell et al. | |
| 6,544,573 | B1 | 4/2003 | Pajela et al. | |
| 6,603,053 | B2 | 8/2003 | Hisanaka | |
| 6,638,527 | B2 | 10/2003 | Gott et al. | |
| 6,696,070 | B2 * | 2/2004 | Dunn | 424/402 |
| 6,803,496 | B2 | 10/2004 | Elder et al. | |
| 6,831,107 | B2 | 12/2004 | Dederen et al. | |
| 6,894,028 | B2 | 5/2005 | Lipton et al. | |
| 7,122,238 | B2 | 10/2006 | Macedo | |
| 7,147,751 | B2 | 12/2006 | Shannon et al. | |
| 7,169,400 | B2 | 1/2007 | Luu et al. | |
| 7,195,771 | B1 | 3/2007 | Hsu et al. | |
| 7,358,279 | B2 | 4/2008 | Goget et al. | |
| 7,365,030 | B2 | 4/2008 | Chamba et al. | |
| 7,416,735 | B2 | 8/2008 | El-Nokaly et al. | |
| 7,592,019 | B2 | 9/2009 | Drucks et al. | |
| 7,651,691 | B2 | 1/2010 | Roso et al. | |
| 7,838,477 | B2 | 11/2010 | Wenzel et al. | |
| 7,951,840 | B2 | 5/2011 | Modak et al. | |
| 2002/0025334 | A1 | 2/2002 | Smith | |
| 2002/0120242 | A1 | 8/2002 | Tyrrell et al. | |
| 2002/0165508 | A1 | 11/2002 | Klofta et al. | |
| 2003/0035785 | A1 | 2/2003 | Palumbo et al. | |
| 2003/0045645 | A1 | 3/2003 | Chang et al. | |
| 2003/0082223 | A1 | 5/2003 | Healy et al. | |
| 2003/0124373 | A1 | 7/2003 | Weuthen et al. | |
| 2003/0165449 | A1 | 9/2003 | Kaczvinsky et al. | |
| 2003/0220042 | A1 | 11/2003 | Lostocco et al. | |
| 2004/0052834 | A1 | 3/2004 | West et al. | |
| 2004/0058073 | A1 | 3/2004 | Bunyard et al. | |
| 2004/0122389 | A1 | 6/2004 | Mace et al. | |
| 2004/0166183 | A1 | 8/2004 | Ruseler-Van et al. | |
| 2004/0242097 | A1 | 12/2004 | Hasenoehrl et al. | |
| 2005/0002994 | A1 | 1/2005 | Goppel et al. | |
| 2005/0008680 | A1 * | 1/2005 | Deckner et al. | 424/443 |
| 2005/0008681 | A1 | 1/2005 | Deckner et al. | |
| 2005/0013790 | A1 | 1/2005 | Yamaki et al. | |
| 2005/0031653 | A1 | 2/2005 | Kwetkat et al. | |
| 2005/0031847 | A1 | 2/2005 | Martens et al. | |
| 2005/0036960 | A1 | 2/2005 | Bussey et al. | |
| 2005/0048105 | A1 | 3/2005 | McNulty et al. | |
| 2005/0058672 | A1 | 3/2005 | Gupta | |
| 2005/0158369 | A1 | 7/2005 | Dorschner et al. | |
| 2006/0159645 | A1 | 7/2006 | Miller et al. | |
| 2006/0171971 | A1 | 8/2006 | Marsh et al. | |
| 2006/0193819 | A1 | 8/2006 | Lu et al. | |
| 2006/0210612 | A1 | 9/2006 | Simon et al. | |
| 2007/0020342 | A1 * | 1/2007 | Modak et al. | 424/642 |
| 2007/0141127 | A1 | 6/2007 | Casas-Sanchez et al. | |
| 2007/0254543 | A1 | 11/2007 | Bunyard et al. | |
| 2008/0145664 | A1 | 6/2008 | Sirovatka et al. | |
| 2008/0146484 | A1 | 6/2008 | Sirovatka et al. | |
| 2008/0207767 | A1 | 8/2008 | Dobos et al. | |
| 2008/0299065 | A1 | 12/2008 | Arditty | |
| 2009/0035229 | A1 | 2/2009 | Eirew | |
| 2009/0035340 | A1 | 2/2009 | Landa et al. | |
| 2009/0081269 | A1 | 3/2009 | Erazo-Majewicz et al. | |
| 2009/0181070 | A1 | 7/2009 | Blease et al. | |
| 2009/0226498 | A1 | 9/2009 | Flugge-Berendes et al. | |
| 2009/0263439 | A1 | 10/2009 | Casas-Sanchez et al. | |
| 2010/0158964 | A1 | 6/2010 | Cunningham et al. | |
| 2011/0033413 | A1 | 2/2011 | Kwetkat et al. | |
| 2011/0224637 | A1 | 9/2011 | Edgett et al. | |
| 2011/0268777 | A1 | 11/2011 | Marsh et al. | |
| 2011/0318434 | A1 | 12/2011 | Guthery | |
| 2012/0090113 | A1 | 4/2012 | Manifold et al. | |
| 2014/0004163 | A1 | 1/2014 | Mundschau et al. | |
| 2014/0004166 | A1 | 1/2014 | Cunningham et al. | |

FOREIGN PATENT DOCUMENTS

| | | | |
|---|---|---|---|
| EP | 0 922 452 | A1 | 6/1999 |
| EP | 0 922 456 | A1 | 6/1999 |
| EP | 1 192 955 | A2 | 4/2002 |
| EP | 1 014 938 | B1 | 7/2002 |
| EP | 1 618 925 | A1 | 1/2006 |
| EP | 1 992 367 | A1 | 11/2008 |
| JP | 01-079108 | A | 3/1989 |
| JP | 01-265019 | A | 10/1989 |
| WO | WO 1997/038735 | A1 | 10/1997 |
| WO | WO 1999/024551 | A1 | 5/1999 |
| WO | WO 1999/042131 | A1 | 8/1999 |
| WO | WO 1999/055303 | A1 | 11/1999 |
| WO | WO 2001/028339 | A2 | 4/2001 |
| WO | WO 2001/062224 | A1 | 8/2001 |
| WO | WO 2002/060502 | A2 | 8/2002 |
| WO | WO 2005/044220 | A1 | 5/2005 |
| WO | WO 2006/081071 | A1 | 8/2006 |
| WO | WO 2007/144814 | A1 | 12/2007 |
| WO | WO 2008/129494 | A1 | 10/2008 |
| WO | WO 2009/125405 | A2 | 10/2009 |

* cited by examiner

STABLE EMULSION FOR PREVENTION OF SKIN IRRITATION AND ITEMS USING SAME

This application claims priority to Provisional Patent Application No. 61/666,382, filed on Jun. 29, 2012. The entirety of Provisional Patent Application No. 61/666,382 is incorporated herein by reference.

BACKGROUND OF THE DISCLOSURE

The present disclosure relates generally to a formulation in the form of an emulsion which includes a combination gum blend and a salt tolerant emulsifier, and items using same. The combination provides physical stability to an emulsion containing both zinc salts and silicone oil. The formulation of the present disclosure is useful for rash prevention and may be applied to the skin with a wipe wetted therewith or by other various means.

Wet wipes have been used for years for convenient skin cleansing between diaper changes. Much headway has been made in creating formulations for wet wipes. Such formulations are in the form of emulsions which provide a vehicle for the application of active ingredients to the skin. Such ingredients may be used to treat and/or prevent diaper rash.

Diaper rash is a form of contact dermatitis which afflicts infants or incontinent persons whose wet and/or soiled absorbent garments are not promptly changed. Because of the practical impossibility of attending promptly to all of a person's needs, even those receiving a high level of care sometimes suffer from diaper rash. It has recently come to be understood that the initial stages of some types of diaper rash are the result of skin irritation caused by contact with digestive enzymes present in feces, particularly trypsin, chymotrypsin and elastase. These enzymes are proteolytic enzymes produced in the gastrointestinal tract to digest food. Similar conditions conducive to skin irritation by proteolytic enzymes present in feces are found in patients having colostomies. Such patients would also benefit from improved treatments to prevent skin irritation due to fecal enzymes.

Silicone oil is a commonly used active ingredient that acts as a skin barrier to prevent diaper rash. While there are several methods to achieve stable emulsions with silicone oil at concentrations compliant with its use as an over-the-counter drug, there are several disadvantages associated with these methods. First, the concentration of emulsifier required to successfully stabilize an emulsion containing the silicone oil, e.g. dimethicone, can be so great that it is cost prohibitive. Second, obtaining a low-viscosity, sprayable solution can be difficult due to the high probability that silicone oil droplets will coalesce, particularly at the elevated temperatures to which the solution may be exposed. Third, without appropriately modifying the rheology of the water phase, emulsions with a low viscosity and low solids content tend to undergo phase separation, particularly following a freeze-thaw cycle. This results in a non-uniform product that would not be efficacious.

Sometimes a skin barrier alone is not enough to prevent diaper rash, especially when fecal matter is present. Therefore, it is also desirable to inhibit skin irritants such as proteolytic enzymes. One way to inhibit such enzymes is to apply a water-soluble zinc salt to the skin. Zinc has long been known to sooth irritated skin/prevent skin irritation. However, zinc salts are not very compatible with silicone oils because when combined together in an emulsion, the emulsion can phase separate due to the increased ionic strength.

Accordingly, there is a need for an emulsion that contains silicone oil as an active ingredient and does not phase separate even in the presence of zinc salts. There is a further need to stabilize an emulsion containing silicone oil in a manner that is cost effective. It would be further advantageous if the emulsion would be suitable for spraying onto a substrate during the manufacture of a wet wipe. In addition, there is a need to preserve the emulsion without causing phase separation, especially if the emulsion is to be applied to a substrate.

BRIEF DESCRIPTION OF THE DISCLOSURE

It has now been unexpectedly found that stable emulsions containing both silicone oil and zinc salts can be formed with a salt-tolerant emulsifier and a gum blend. In particular, the gum blend contains one or more gums and propylene glycol alginate. One or more of the following gums may be suitable: xanthan gum, guar gum, gellan gum, acacia gum, cellulose gum, dehydroxanthan gum, *sclerotium* gum and locust bean gum. The emulsion is not only stable, but has a viscosity that is low enough to be sprayable for the purpose of applying it to a wipe substrate.

Without being bound by theory, it is believed that propylene glycol alginate in combination with one or more gums provide improved freeze-thaw stability by not only increasing the density of the water phase, but by imparting additional emulsification. Further, the gums are also salt tolerant as opposed to typical rheology modifiers like acrylates, carbomer, polyquaternium-37, etc.

An emulsion for the prevention of skin irritation, the emulsion including: a salt-tolerant emulsifier;

a gum blend comprising a gum and propylene glycol alginate, wherein the gum blend is 0.01% to 0.5% by weight of the emulsion; 1% to 10% by weight silicone oil; 90% to 98% by weight water; and 0.20 to 10% by weight water-soluble zinc salt. The emulsion may be applied to a substrate.

Advantages of the composition of the present disclosure include at least the following: cost effectiveness due to lower concentrations of emulsifier, the capability of being applied to a wipe substrate by spraying, and physical stability.

DETAILED DESCRIPTION OF THE DISCLOSURE

The present disclosure is directed to an emulsion used for the prevention of skin irritation including among other ingredients, an "emulsifier system". The emulsifier system is an emulsifier in combination with a gum blend and propylene glycol alginate. Surprisingly, the emulsion, with its emulsifier system, stays physically stable when water-soluble zinc salts and dimethicone (about 1% to about 10% by weight) are combined in the emulsion.

Generally, the emulsion of the present disclosure contains a carrier medium, a barrier composition, an emulsifier system, and a stability enhancing system. Additional ingredients, e.g. fragrance, botanicals, pH adjusting agents, buffers, preservatives, moisturizers and the like may be added to the emulsion.

Carrier Medium:

Desirably, water serves as a medium for carrying the silicone oil and zinc salts to the skin in an esthetically pleasing manner and at a suitable viscosity as discussed herein. In addition, water aids in the wetting of the substrate of the wipe product incorporating the emulsion. Typically, the emulsions of the present disclosure include from about 90% by weight to about 98% by weight water, including from about 92% by weight to about 97% by weight, and including from about 94% by weight to about 96% by weight.

Barrier Composition:

The emulsions include a barrier composition that serves to protect the skin from the digestive enzymes. Barrier composition components include silicone oils and water-soluble zinc salts.

Silicone Oil

The emulsions of the present disclosure include silicone oil sometimes referred to as polymerized dimethylsiloxane. The silicone oil is an active ingredient that functions primarily as a skin protectant as it provides a barrier against moisture (urine, sweat and overall humidity), and secondarily as an emollient. Desirable silicone oils are those that impart a tactile impression of softness and smoothness, and which do not impart an excessive tactile perception of greasiness, oiliness or coating when incorporated into the emulsion. Non-volatile silicone oils may be desirable over volatile silicone oils. Non-volatile silicone oils tend to remain stable when exposed to the environment, tend to provide a lasting tactile impression and tend to form a stable oil layer on the skin. Mixtures of silicone oils may be used. For example, volatile silicone oils may be combined with non-volatile silicone oils to impart desired esthetic properties, as long as the emulsion contains sufficient non-volatile silicone to provide a skin barrier layer that is effective for a given application.

In one aspect, the silicone oil is dimethicone (linear polydimethylsiloxane). In this aspect of the disclosure, the emulsions of the present disclosure include from about 1% by weight to about 10% by weight dimethicone, including from about 1% by weight to about 5% by weight, and including from about 1% by weight to about 3% by weight. Other exemplary silicone oils that are suitable for use herein include dimethiconol, ethoxylated dimethicone (linear and pendant varieties), amodimethicone and derivatives thereof, cyclomethicone, alkyl substituted derivatives such as stearyl dimethicone and behenyl dimethicone, phenyl trimethicone and mixtures thereof. Such silicones are commercially available, for example, from the Dow Corning Company of Midland, Mich. under the names XIAMETER PMX-200 Silicone Fluid (Dimethicone), XIAMETER PMX-1184 Silicone Fluid (Trisiloxane and Dimethicone), DOW CORNING 1403 Fluid (Dimethicone and Dimethiconol), DOW CORNING 1501 Fluid (Cyclopentasiloxane and Dimethiconol), DOW CORNING 593 Fluid (Dimethicone and Trimethylsiloxysilicate), DOW CORNING 2502 Fluid (Cetyl Dimethicone), and DOW CORNING 558 Fluid (Phenyl Trimethicone).

Zinc Salt

In one aspect of the present disclosure, desired sources of zinc ions are zinc chloride and zinc sulfate. In other aspects of the present disclosure, sources of zinc ions include non-covalent zinc compounds such as zinc acetate, zinc carbonate, zinc nitrate, zinc phosphate, zinc hydroxide, zinc fluoride, zinc bromide, zinc iodide, zinc sulfite, zinc citrate, zinc lactate, zinc salicylate, zinc gluconate, zinc glycinate, zinc glutamate, and zinc stearate. Zinc oxide, a covalent zinc compound, is specifically excluded.

Desirably, the zinc compounds, salts, are about 0.20% to about 10% by weight of the emulsion.

Emulsifier System:

In addition to the carrier and the barrier composition, the emulsions of the present disclosure include an emulsifier system for forming oil-in-water emulsions. The emulsifier system is a synergistic combination of specific ingredients which stabilize other formulation components that would not otherwise mix together in a stable manner. It is capable of de-emulsifying upon application of the complete formulation to the skin thereby delivering a silicone oil film on the skin. The emulsifier system does not tend to re-emulsify once the emulsion is applied to the skin and exposed to urine or other body fluids. This prevents the silicone oil from being washed away when an insult occurs.

Specifically, the emulsifier system contains a select group of phosphate esters along with two additional components, (a) a salt-tolerant emulsifier and (b) a gum-blend.

Salt-Tolerant Emulsifier

A desirable emulsifying agent based on phosphate esters is similar in structure to the phospholipids found in the skin. Hence, it is substantive and compatible with the skin's natural lipids. Like phospholipids, dialkyl phosphate esters have surfactant characteristics that tend to promote the formation of bilayers or lamellar structures.

Emulsifying agents based on phosphate esters are formed by reacting phosphoric acid or its derivatives with a fatty alcohol(s), such as cetearyl alcohol, cetyl alcohol, or behenyl alcohol resulting in an anionic compound. Phosphate esters are well known for their ability to retain active ingredients of interest, such as sunscreens or, in the present invention, ingredients to protect the skin from environmental insults, such as fecal enzymes. As described herein, select anionic phosphate ester emulsifiers were compatible with zinc salts, which disperse cationic zinc ions when dissolved in the emulsion.

Desirably, the phosphate ester linkage is very stable at high and low pH, giving it extreme pH tolerance. The emulsion characteristic of the ester depends on the degree of neutralization of the free acid groups.

The phosphate ester is a mid-range HLB emulsifier that is used to achieve low viscosity dispersions of small and uniform particles. It produces stable and well-dispersed systems even in products that contain a relatively high load of pigments and oils. The phosphate ester maintains consistency over time and is much less sensitive to shear rate. Further, it forms emulsions without foaming and can easily be incorporated into the oil phase. Generally, phosphate esters are used as primary emulsifying agents for formulations at weight percentages of 0.5% to 5%. Additionally, phosphate esters can also be incorporated at lower levels as co-emulsifiers. Phosphate ester is present in a desired amount of about 0.5 to about 3% by weight of the emulsion, and even more desirably about 0.75% to about 2% by weight of the emulsion.

In one aspect of the disclosure, a desired phosphate ester is available from Croda Inc. as CRODAFOS CS20A.

Gemini Surfactants

Gemini surfactants are a special class of surfactants that contains multiple hydrophobic tails and multiple hydrophilic head groups within the same molecule. Gemini surfactants can be ten to a thousand times more surface active than conventional surfactants with similar but single hydrophilic and hydrophobic groups in the molecule. Gemini surfactants may reduce skin irritation in addition to serving as an emulsifier.

Many Gemini surfactants were explored in an effort to create a stable emulsion containing dimethicone and clay, surprisingly, the only Gemini surfactant that was found to work in an emulsion having 95.15% water was Disodium Ethylene Dicocamide PEG-15 Disulfate. In one aspect of the disclosure the Gemini surfactant is blended with Behenyl Alcohol, Glyceryl Stearate and Glyceryl Stearate Citrate, and is available in this form from Sasol North America, Inc. as CERALUTION H. The Gemini surfactant is limited to the oil phase.

Gemini surfactants are believed to form liquid crystalline lamellar gel networks in the oil phase which result in the formation of very small oil droplets. The small size and gel-like nature of the droplets provides resistance against coalescence of the droplets eventuating in complete oil phase separation. In addition, Gemini surfactants have been shown to not have the HLB dependency for oil emulsification of typical ethoxylated fatty alcohols, ethoxylated fatty esters, and other common non-Gemini emulsifiers.

Stability Enhancing System:

The stability enhancing system is a gum blend which includes a single gum or multiple gums and propylene glycol alginate. One desirable gum blend is made from xanthan gum and guar gum. In certain applications, it may be advantageous to substitute the xanthan gum and/or guar gum with gellan gum, acacia gum, cellulose gum, dehydroxanthan gum, *sclerotium* gum or locust bean gum.

Without being bound by theory, it is believed that propylene glycol alginate improves freeze-thaw stability by not only increasing the density of the water phase, but by imparting additional emulsification of the silicone oil.

Desirably, the gum blend is used in an amount between about 0.01% to about 0.5% by weight of the emulsion.

Gums are rheological modifiers. Other classes of rheological modifiers such as starches may be used in combination with propylene glycol alginate provided that a stable emulsion is achieved using less than 0.5% by weight rheological modifiers and the viscosity of the formulation measures below 5,000 cps as obtained using a Brookfield DV-II Viscometer with spindle 5 at 6 r.p.m.

Optional Ingredients:

1) pH Adjusting Agent

The emulsions of the present disclosure may further include a pH-adjusting agent. Such agents are desirable for the creation of emulsions that have a pH at or near that of human skin. Therefore, the pH will typically be adjusted as may be necessary to provide the emulsion of the present disclosure with a pH of from 4 to 7, more preferably from 4.5 to 6.5. The pH can be adjusted by adding one or more pH-adjusting agents in an amount effective to provide such pH values ("effective amount"). Agents that may be used to adjust the pH of the emulsions include organic and inorganic acids and bases. In one aspect of the present disclosure, a more desirable pH-adjusting agent is malic acid.

For the more desirable emulsions of the present disclosure, the emulsion in the absence of a pH-adjusting agent tends to be more basic than desired. Therefore, an acid pH-adjusting agent will typically be used to bring the emulsion to the desired pH. Acid pH-adjusting agents include organic acids, desirably that are relatively non-irritating. Such acids include malic acid, citric acid acetic acid, propionic acid, oxalic acid, glycolic acid, malonic acid, lactic acid, succinic acid, tartaric acid, aspartic acid, maleic acid, glutaric acid, glutamic acid, gluconic acid, sorbic acid, benzoic acid, ascorbic acid, salicylic acid and mixtures thereof.

The amount of the pH-adjusting agent that is employed depends on the equivalent weight of the pH-adjusting agent and the desired pH. Typically, the pH-adjusting agent is used in an amount of from about 0.05% to about 0.5% by weight of the emulsion. Desirable emulsions of the present disclosure include from about 0.1% to about 0.5% percent, typically about 0.2% to about 0.3% percent the pH-adjusting agent.

2) Preservatives

Preservatives function in one or more ways to improve the shelf life of the emulsions and products incorporating same. For example, the preservative may be an anti-microbial agent, an anti-bacterial agent, an anti-fungal agent, or a combination thereof.

Anti-microbial agents herein include, but are not limited to, benzethonium chloride, benzisothiazolinone, benzoic acid, benzyl alcohol, 2-Bromo-2-nitropropane-1,3-diol, butylparaben, caprylyl glycol, chlorhexidine digluconate, DMDM hydantoin, diazolidinyl urea, dehydroacetic acid, ethylparaben, iodopropynyl butylcarbamate, methylchloroisothiazolinone, methylisothiazolinone, methyldibromo glutaronitrile, Methylparaben, Pentylene glycol, phenethyl alcohol, phenoxyethanol, propylparaben, polyaminopropyl biguanide, quaternium-15, salicylic acid, sodium benzoate, sodium methylparaben, sodium dehydroacetate, thymol, triclosan and mixtures thereof.

In one aspect of the disclosure, benzoic acid is used with or without phenoxyethanol. These compounds are effective in preventing the growth of a wide variety of microbes, and are efficacious against the growth of fungi. Protecting against microbes and fungi tends to be particularly desirable where the wipe product contains a porous substrate, for example, nonwoven substrates.

Desirably, wet wipes have a shelf life of at least two years under storage conditions of about 75 degrees Fahrenheit and 50 percent relative humidity. Certain agents may be employed to achieve the desired term, one of which is an anti-microbial agent. The anti-microbial agent may be used in an amount that is effective to provide the desired shelf life (storage stability, i.e., microorganisms do not grow to a significant extent) (herein alternatively referred to as "an effective amount"). This includes demonstrating sufficient anti-microbial activity in accordance with United States Pharmacopeia test entitled "Microbial Test, Antimicrobial Preservative-Effectiveness".

3) Other

The emulsion of the present disclosure may optionally include other ingredients, e.g., fragrance; skin soothing aids such as aloe, lavender, chamomile, green tea, calendula, etc.; skin moisturizers (humectants) such as glycerin, propylene glycol, betaine, and hydroxyethyl urea; or emollients other than those previously described; powders and the like.

Viscosity:

While the examples herein show a highly aqueous emulsion, it is noted that emulsions with lower levels of water and thus higher viscosities may be desired, especially when applied to the skin by means other than a wet wipe. For instance, the emulsion may be formulated to be a lotion, gel or paste. However, for application to wipe substrates as disclosed herein, it is desirable to have a viscosity at 25 degrees Celsius of about 5000 centipoise (cps) or less, or in other applications, 4000 cps or less as obtained using a Brookfield DV-II Viscometer with spindle 5 at 6 r.p.m.

EXAMPLES

Table 1: Stable, Highly Aqueous Low-Viscosity Dimethicone Emulsions.

Table 2: Effect of 0.9% Zinc Chloride on Emulsion Stability.

Table 3: Effect of Zinc Chloride Concentration on Stability of Emulsion Stability.

Table 4: Effect of Zinc Sulfate Concentration on Stability of Emulsion Stability.

TABLE 1

| Trade Name | INCI Name | F1 | F2 | F3 | F4 | F5 | F6 | F7 | F8 | F9 | F10 |
|---|---|---|---|---|---|---|---|---|---|---|---|
| Part A | | | | | | | | | | | |
| Water | Water | 95.15 | 95.15 | 95.15 | 95.15 | 95.15 | 95.15 | 95.15 | 95.15 | 94.15 | 94.15 |
| ARAGUM 3173 | Xanthan Gum (and) Guar Gum (and) Propylene Glycol Alginate | 0.50 | 0.50 | 0.50 | 0.50 | 0.50 | 0.50 | 0.50 | 0.50 | 0.50 | 0.50 |
| PART B | | | | | | | | | | | |
| CETIOL 868 | Ethylhexyl Stearate | 0.50 | 0.50 | 0.50 | 0.50 | 0.50 | 0.50 | 0.50 | 0.50 | 0.50 | 0.50 |
| CETIOL SN | Cetearyl Isononanoate | 0.50 | 0.50 | 0.50 | 0.50 | 0.50 | 0.50 | 0.50 | 0.50 | 0.50 | 0.50 |
| DC 200, 100 CST | Dimethicone | 1.50 | 1.50 | 1.50 | 1.50 | 1.50 | 1.50 | 1.50 | 1.50 | 1.50 | 1.50 |
| MONTANOV 202 | Arachidyl Alcohol (and) Behenyl Alcohol (and) Arachidyl Glucoside | 1.00 | — | — | — | — | — | — | — | — | — |
| MONTANOV 68 | Cetearyl Alcohol (and) Cetearyl Glucoside | — | 1.00 | — | — | — | — | — | — | — | — |
| MONTANOV 82 | Cetearyl Alcohol (and) Coco-Glucoside | — | — | 1.00 | — | — | — | — | — | — | — |
| MONTANOV S | Coco-Glucoside (and) Coconut Alcohol | — | — | — | 1.00 | — | — | — | — | — | — |
| MONTANOV L | C14-22 Alcohols (and) C12-20 Alkyl Glucoside | — | — | — | — | 1.00 | — | — | — | — | — |
| OLIVEM 1000 | Cetearyl Olivate (and) Sorbitan Olivate | — | — | — | — | — | 1.00 | — | — | — | — |
| INCROQUAT BEHENYL TMS-50 | Behentrimonium Methosulfate (and) Cetyl Alcohol (and) Butylene Glycol | — | — | — | — | — | — | 1.00 | — | — | — |
| PROLIPID 151 | Stearic Acid (and) Behenyl Alcohol (and) Glyceryl Stearate (and) Stearyl Alcohol (and) Cetyl Alcohol (and) Palmitic Acid (and) Hydroxyethyl Cetearamidopropyldimonium Chloride (and) Myristyl Alcohol | — | — | — | — | — | — | — | 1.00 | — | — |
| AMPHISOL A | Cetyl Phosphate | — | — | — | — | — | — | — | — | 1.00 | — |
| CERALUTION H | Behenyl Alcohol (and) Glyceryl Stearate (and) Glyceryl Stearate Citrate (and) Disodium Ethylene Dicocamide PEG-15 Disulfate | — | — | — | — | — | — | — | — | — | 2.00 |
| PART C | | | | | | | | | | | |
| PUROX S | Sodium Benzoate | 0.45 | 0.45 | 0.45 | 0.45 | 0.45 | 0.45 | 0.45 | 0.45 | 0.45 | 0.45 |
| BRONIDOX 1160 | Phenoxyethanol | 0.40 | 0.40 | 0.40 | 0.40 | 0.40 | 0.40 | 0.40 | 0.40 | 0.40 | 0.40 |

TABLE 2

| Primary Emulsifier | F/T Stable | 50 C. Stable-1 Week | 40 C. Stable-3 Months |
|---|---|---|---|
| MONTANOV 202 | No | Yes | No |
| MONTANOV 68 | No | No | No |
| MONTANOV 82 | Yes | No | No |
| MONTANOV S | Yes | No | No |
| MONTANOV L | No | No | No |
| OLIVEM 1000 | No | No | NA |

TABLE 2-continued

| Primary Emulsifier | F/T Stable | 50 C. Stable-1 Week | 40 C. Stable-3 Months |
|---|---|---|---|
| INCROQUAT BEHENYL TMS-50 | No | Yes | NA |
| PROLIPID 151 | No | No | No |
| AMPHISOL A | Yes | No | No |
| CERALUTION H | Yes | Yes | Yes |

TABLE 3

| | Weight Percent of Zinc Chloride Added (%) | | | | | | | |
|---|---|---|---|---|---|---|---|---|
| | 0% | 0.42% | 0.63% | 0.83% | 1.04% | 1.25% | 1.67% | 2.08% |
| Freeze/Thaw Stable | No | No | No | No | No | No | No | No |
| 40 C. Stable (3 Months) | Yes | Yes | Yes | Yes | Yes | Yes | Yes | No |

TABLE 3-continued

| | Weight Percent of Zinc Chloride Added (%) | | | | | | | |
|---|---|---|---|---|---|---|---|---|
| | 0% | 0.42% | 0.63% | 0.83% | 1.04% | 1.25% | 1.67% | 2.08% |
| 5 C. Stable (3 Months) | Yes | Yes | Yes | Yes | Yes | Yes | Yes | Yes |

TABLE 4

| | Weight Percent of Zinc Sulfate Added (%) | | | | | | | |
|---|---|---|---|---|---|---|---|---|
| | 0% | 0.55% | 0.82% | 1.10% | 1.37% | 1.65% | 2.20% | 2.75% |
| Freeze/Thaw Stable | Yes | Yes | Yes | Yes | Yes | No | No | No |
| 40 C. Stable (3 Months) | Yes | Yes | Yes | Yes | Yes | Yes | Yes | No |
| 5 C. Stable (3 Months) | Yes | Yes | Yes | Yes | Yes | Yes | Yes | Yes |

Table 1 lists ten emulsions (F1-F10) that demonstrated adequate stability following freeze/thaw testing according to the methods described herein. Generally, stability of the emulsion was tested for a minimum of four weeks at 50 degrees Celsius, three months at 40 degrees Celsius and 5 degrees Celsius. Three Freeze/thaw cycles are listed in Table 1 below. Three freeze/thaw cycles were applied to each emulsion at these two different temperatures.

In addition to the emulsifiers provided in Table 1, additional emulsifiers were screened between 1% and 3% by weight alone or in combination with one another with the other ingredients remaining constant in the emulsion. Emulsifiers that failed to produce a stable emulsion include: Glyceryl Stearate, Glyceryl Stearate/PEG-100 Stearate, Sorbitan Sesquioleate, Sorbitan Olivate, Undeceth-3, PEG-20 Methyl Glucose Sesquistearate, Trideceth-3, Trideceth-12, Laureth-9, Behenoyl Stearic Acid, Oleth-2, Oleth-20, Sorbitan Laurate, Sorbitan Palmitate, Sorbitan Oleate, Sorbitan Trioleate, Steareth-2, Steareth-20, Steareth-21, Laureth-23, C11-15 Pareth-15, PPG-24-Buteth-27, High molecular weight polymers of ethylene oxide and propylene oxide, PPG-5-Ceteth-10 Phosphate, Oleth-5 Phosphate, Dioleyl Phosphate, Oleth-3 Phosphate, Oleth-10 Phosphate, Lauryl Phosphate, Trideceth-3 Phosphate, Trideceth-6 Phosphate, Deceth-6 Phosphate, Trilaureth-4 Phosphate, C20-22 Alkyl Phosphate, C20-22 Alcohols, Polyglyceryl-10 Decaoleate, Polyglyceryl-3 Oleate, PEG/PPG-20/6 Dimethicone, Bis-PEG/PPG-20/20 Dimethicone, Bis-PEG/PPG-16/16 PEG/PPG-16/16 Dimethicone, Bis-PEG/PPG-20/5 PEG/PPG-20/5 Dimethicone, Methoxy PEG/PPG-25/4 Dimethicone, Bis-PEG/PPG-14/14 Dimethicone (and) Dimethicone, PEG-11 Methyl Ether Dimethicone, PEG/PPG-20/22 Butyl Ether Dimethicone, Lauryl PEG-9 Polydimethylsiloxyethyl Dimethicone, PEG-10 Dimethicone, Polyglyceryl-3 Disiloxane Dimethicone, Lauryl Polyglyceryl-3 Polydimethylsiloxyethyl Dimethicone, Lauryl PEG-8 Dimethicone, Sodium Stearate, Sucrose Laurate, Sucrose Myristate, Sucrose Stearate and Methyl Glucose Sesquistearate. Unexpectedly, use of Disodium Ethylene Dicocamide PEG-15 Disulfate as the only Gemini surfactant in a system containing 94.15% water produced a stable emulsion.

In general, the procedure for making the emulsions is as follows:
1. Heat the water phase of the formulation to 75 degrees Celsius while slowly adding the gum blend.
2. Combine materials of the oil phase of the formulation and heat them to 75 degrees Celsius under conditions of constant mixing.
3. Add the oil phase to the water phase and homogenize the mixture at 5000 to 7000 rpm for five minutes using a SILVERSON homogenizer available from Silverson Machines, Inc.
4. Cool the mixture to 35 degrees Celsius under conditions of constant mixing.
5. Add preservatives if desired.
6. Adjust pH to 4.5+/−0.5 using an acid.
7. Homogenize the mixture again for two minutes at 2000 to 3000 rpm.

Additional testing demonstrated one way to achieve a stable low viscosity formulation through three freeze-thaw cycles at elevated temperatures was through use of a combination of one or more gums and propylene glycol alginate. This combination is present in a concentration greater than 0.05% such that the aggregate sum of these components do not exceed 0.50% weight of the finished formulation. Additional water phase rheology modifiers that were evaluated alone or in combination with other rheology modifiers but did not produce a stable emulsions include: Citrus Aurantium Sinensis (Orange) Fiber, Acacia Seyal Gum Octenylsuccinate, Behenoxy PEG-10 Dimethicone, Bentonite, Disteareth-75 IPDI, Galactoarabinan, gums (Gellan Gum, Guar gum, Cellulose Gum and Gum Acacia) that are not in combination with propylene glycol alginate, Hydroxyethyl Cellulose, Hydroxypropyl Starch Phosphate, Laponite XLS, Magnessium Aluminum Silicate, Microcrystalline Cellulose, Montmorillonite, PEG-150 Distearate, PEG-175 Diisostearate, PEG-20 Methyl Glucose Sesquistearate, Polyacrylate Crosspolymer-6, Potato Starch Modified, Propylene Glycol Alginate, Sodium Alginate, Sodium Aluminum Silicate, Sodium Carboxymethylcellulose, Tromethamine Magnesium Aluminum Silicate and Xanthan Gum.

Emulsions F1-F10 included 0.9% by weight Zinc Chloride in an effort to determine whether the previously stable base would remain stable through 3 freeze thaw cycles and 50 degrees Celsius for a minimum of 2 weeks. As shown by Table 2 below, surprisingly, only the formulation containing Ceralution H with a combination of Xanthan Gum, Guar Gum and Propylene Glycol Alginate remained stable when exposed to the aforementioned stability conditions. It is known that ionic materials can negatively impact the stability provided by polysaccharide materials for sprayable, low viscosity emulsions (See, U.S. Pat. No. 6,831,107).

A subsequent dosage study using zinc chloride or zinc sulfate with Formulation 10 demonstrated that a significant amount of zinc could be added to the formulation and remain stable. The results of this study are shown in Tables 3 and 4.

As shown in Tables 3 and 4, emulsions with Zinc Sulfate had superior freeze/thaw stability performance compared to solutions with Zinc Chloride. Following three months at 40 degrees Celsius, the viscosity of all of the above emulsions remained between 1000 and 5000 centipoise as measured with a Brookfield viscometer (RV Spindle 5, 6 rpm) available from Brookfield Engineering Laboratories.

Similar stability results were obtained with emulsions containing 1% CRODAFOS CS20A available from Croda Inc.)

Wipe Substrates and Emulsion Add-On Levels

As used herein, the term "substrate" means any material suitable for carrying the emulsion of the present disclosure. Suitable substrates include any material that does not hinder the deposition of desirable emulsion components onto the skin, and does not cause skin irritation.

Examples of suitable substrates include, but are not limited to, woven or non-woven webs, spunbonded fabric, meltblown fabric, knit fabric, wet-laid fabric, scrims, needle-punched webs, synthetic fibers and natural fibers. It is to be understood that these suitable substrates are not mutually exclusive and can be used in a combination.

The choice of substrate fibers depends upon, for example, fiber cost and the desired properties. For example suitable fibrous materials may include, but are not limited to, synthetic fibers such as those derived from polyolefins, polyesters, polyamides, polyacrylics, polyethylene, polypropylene, polyvinyl, etc., alone or in combination with one another. Similarly, natural fibers such as cotton, linen, hemp, jute, wool, wood pulp, etc.; regenerated cellulosic fibers such as viscose rayon and cuprammonium rayon or modified cellulosic fibers, such as cellulose acetate may likewise be used. Blends of one or more of the above fibers may also be used if so desired.

As used herein, the term "nonwoven fabric" refers to a fabric having a structure of individual fibers or filaments which are randomly and/or unidirectionally interlaid in a mat-like fashion. Nonwoven fabrics can be made from a variety of processes including, but not limited to, air-laid processes, wet-laid processes, hydroentangling processes, staple fiber carding and bonding, and solution spinning. Suitable nonwoven fabrics include, but are not limited to, spunbonded fabrics, meltblown fabrics, wet-laid fabrics and combinations thereof.

As used herein, the term "spunbonded fabric" refers to a web of small diameter fibers and/or filaments which are formed by extruding a molten thermoplastic material, or coextruding more than one molten thermoplastic material, as filaments from a plurality of fine, usually circular, capillaries in a spinnerette with the diameter of the extruded filaments then being rapidly reduced, for example, by non-eductive or eductive fluid-drawing or other well-known spunbonding mechanisms. The production of spunbonded nonwoven webs is well-known and illustrated in patents such as Appel, et al., U.S. Pat. No. 4,340,563; Dorschner et al., U.S. Pat. No. 3,692,618; Kinney, U.S. Pat. Nos. 3,338,992 and 3,341,394; Levy, U.S. Pat. No. 3,276,944; Petersen, U.S. Pat. No. 3,502,538; Hartman, U.S. Pat. No. 3,502,763; Dobo et al., U.S. Pat. No. 3,542,615; and Harmon, Canadian Pat. No. 803,714.

As used herein, the term "meltblown fabrics" refers to a fabric comprising fibers formed by extruding a molten thermoplastic material through a plurality of fine, usually circular, die capillaries as molten threads or filaments into a high velocity gas (e.g. air) stream which attenuates the filaments of molten thermoplastic material to reduce their diameters, which may be to microfiber diameter. Thereafter, the meltblown fibers are carried by the high-velocity gas stream and are deposited on a collecting surface to form a web of randomly disbursed meltblown fibers. The meltblown process is well-known and is described in various patents such as U.S. Pat. No. 3,849,241 to Butin, et al.

As used herein, the term "microfibers" means small diameter fibers having an average diameter not greater than about 100 microns, for example, having a diameter of from about 0.5 microns to about 50 microns. More specifically microfibers may also have an average diameter of from about 1 micron to about 20 microns. Microfibers having an average diameter of about 3 microns or less are commonly referred to as ultra-fine microfibers.

As used herein, the term "wet-laid fabrics" refers to fabrics formed by a process, such as a paper-making process, wherein fibers dispersed in a liquid medium are deposited onto a screen such that the liquid medium flows through the screen, leaving a fabric on the surface of the screen. Fiber bonding agents may be applied to the fibers in the liquid medium or after being deposited onto the screen. Wet-laid fabrics may contain natural and/or synthetic fibers.

As used herein, the term "spunlaced fabrics" refers to a web of material consisting of a blend of natural fibers and synthetic fibers, where the fibers are subjected to high-velocity water jets which entangle the fibers to achieve mechanical bonding. Desirably, the natural fibers are wood pulp fibers and the synthetic fibers are polyester fibers.

As used herein, the terms "needle-punched" and "needled" refer to a web of material consisting of one or more fibrous materials, wherein the fibers are subjected to needles which entangle the fibers to achieve mechanical interlocking without the need for adhesives or chemical additives.

As used herein, the term "woven fabric" refers to a fabric containing a structure of fibers, filaments or yarns, which are orderly arranged in an interengaged fashion. Woven fabrics typically contain interengaged fibers in a "warp" and "fill" direction. The warp direction corresponds to the length of the fabric while the fill direction corresponds to the width of the fabric. Woven fabrics can be made on a variety of looms including, but not limited to, shuttle looms, Rapier looms, projectile looms, air jet looms and water jet looms.

The composition of the present disclosure formulation may be incorporated into the basesheet in an add-on amount of from about 50% (by weight of the basesheet) to about 800% (by weight of the basesheet). More specifically, the formulations may be incorporated into the basesheet in an add-on amount of from about 200% (by weight of the basesheet) to about 600% (by weight of the basesheet) or from about 300% (by weight of the basesheet) to about 600% (by weight of the basesheet). The formulation add-on amounts may vary depending on the composition of the basesheet.

Experimental Methods:

Stability Test

The purpose of this test is to demonstrate formulation stability after exposure to potential freezing conditions such as during shipping or storage. The test is performed by freezing the composition at 20 degrees Celsius. Once frozen, the emulsion is allowed to completely thaw at room temperature. This freeze-thaw cycle is conducted for a total of three times. The test results are determined by visual inspection of the emulsion for phase separation.

When introducing elements of the present disclosure or the preferred embodiment(s) thereof, the articles “a”, “an”, “the” and “said” are intended to mean that there are one or more of the elements. The terms “comprising”, “including” and “having” are intended to be inclusive and mean that there may be additional elements other than the listed elements.

In view of the above, it will be seen that the several objects of the disclosure are achieved and other advantageous results attained.

As various changes could be made in the above formulations without departing from the scope of the disclosure, it is intended that all matter contained in the above description shall be interpreted as illustrative and not in a limiting sense.

The invention claimed is:

1. An emulsion for the prevention of skin irritation, the emulsion comprising:
- a salt-tolerant emulsifier;
- a gum blend comprising a gum and propylene glycol alginate, wherein the gum blend is 0.01% to 0.5% by weight of the emulsion;
- 1% to 10% by weight silicone oil;
- 90% to 98% by weight water;
- 0.20% to 10% by weight water-soluble zinc salt,
- a pH adjusting agent in an amount to bring the emulsion to a pH of 4 to 7, and
- a preservative selected from the group consisting of phenoxyethanol, benzethonium chloride, benzisothiazolinone, benzyl alcohol, 2-Bromo-2-nitropropane-1,3-diol, butylparaben, caprylyl glycol, chlorhexidine digluconate, DMDM hydantoin, diazolidinyl urea, dehydroacetic acid, ethylparaben, iodopropynyl butylcarbamate, methylchloroisothiazolinone, methylisothiazolinone, methyldibromo glutaronitrile, methylparaben, pentylene glycol, phenethyl alcohol, phenoxyethanol, propylparaben, polyaminopropyl biguanide, quaternium-15, salicylic acid, sodium methylparaben, sodium dehydroacetate, thymol, triclosan and mixtures thereof.

2. The emulsion of claim 1 wherein the salt-tolerant emulsifier comprises a phosphate ester and/or a Gemini surfactant limited to the oil phase.

3. The emulsion of claim 1 wherein the silicone oil consists of dimethicone.

4. The emulsion of claim 1 wherein the silicone oil is selected from the group consisting of dimethicone, amodimethicone and derivatives thereof, dimethiconol, cyclomethicone, stearyl dimethicone, behenyl dimethicone, phenyl trimethicone and combinations thereof.

5. The emulsion of claim 1 having a viscosity of less than 5000 centipoise.

6. The emulsion of claim 1 wherein the gum consists of xanthan gum and guar gum.

7. The emulsion of claim 1 wherein the gum is selected from the group consisting of xanthan gum, guar gum, gellan gum, acacia gum, cellulose gum, dehydroxanthan gum, *sclerotium* gum, locust bean gum and combinations thereof.

8. A wet wipe comprising a substrate with the emulsion of claim 6 deposited thereon.

9. A wet wipe comprising:
- a substrate having an emulsion deposited thereon, the emulsion comprising:
- a salt-tolerant emulsifier;
- a gum blend comprising a gum and propylene glycol alginate, wherein the gum blend is 0.01% to 0.5% by weight of the emulsion;
- 1% to 10% by weight silicone oil;
- 90% to 98% by weight water;
- at least 0.25% by weight water-soluble zinc salt,
- a pH adjusting agent in an amount to bring the emulsion to a pH of 4 to 7, and
- a preservative selected from the group consisting of phenoxyethanol, benzethonium chloride, benzisothiazolinone, benzyl alcohol, 2-Bromo-2-nitropropane-1,3-diol, butylparaben, caprylyl glycol, chlorhexidine digluconate, DMDM hydantoin, diazolidinyl urea, dehydroacetic acid, ethylparaben, iodopropynyl butylcarbamate, methylchloroisothiazolinone, methylisothiazolinone, methyldibromo glutaronitrile, methylparaben, pentylene glycol, phenethyl alcohol, phenoxyethanol, propylparaben, polyaminopropyl biguanide, quaternium-15, salicylic acid, sodium methylparaben, sodium dehydroacetate, thymol, triclosan and mixtures thereof.

10. The wet wipe of claim 9 wherein the gum is selected from the group consisting of xanthan gum, guar gum, gellan gum, acacia gum, cellulose gum, dehydroxanthan gum, *sclerotium* gum, locust bean gum and combinations thereof.

11. The wet wipe of claim 9 wherein the silicone oil is selected from the group consisting of dimethicone, amodimethicone and derivatives thereof, dimethiconol, cyclomethicone, stearyl dimethicone, behenyl dimethicone, phenyl trimethicone and combinations thereof.

12. The wet wipe of claim 9 wherein the emulsion contains 94% to 98% by weight water.

13. The wet wipe of claim 9 wherein the gums are xanthan gum and guar gum, and the silicone oil is dimethicone.

14. The wet wipe of claim 9 wherein the substrate is a non-woven material.

15. The wet wipe of claim 9 wherein the substrate comprises woven fabric, spunbonded fabric, meltblown fabric, knit fabric, wet-laid fabric, scrims or needle-punched webs.

* * * * *